United States Patent [19]

Bigg

[11] 4,431,648

[45] * Feb. 14, 1984

[54] NEW THERAPEUTICALLY USEFUL PHENETHYL DERIVATIVES OF THIAZOLE

[75] Inventor: Dennis Bigg, Jouy-en-Josas, France

[73] Assignee: Synthelabo, Paris, France

[*] Notice: The portion of the term of this patent subsequent to Sep. 14, 1999 has been disclaimed.

[21] Appl. No.: 394,881

[22] Filed: Jul. 2, 1982

[30] Foreign Application Priority Data

Jul. 3, 1981 [FR] France .................................. 81 13078

[51] Int. Cl.³ ................. C07D 513/04; A61K 31/425; A61K 31/505

[52] U.S. Cl. .................................... 424/251; 424/270; 544/278; 548/154

[58] Field of Search ................ 548/154; 424/270, 251; 544/278

[56] References Cited

U.S. PATENT DOCUMENTS 3,806,515 4/1974 Houlihan ........................... 548/154
4,349,557 9/1982 Bigg .................................. 548/154

*Primary Examiner*—Robert Gerstl
*Attorney, Agent, or Firm*—Wegner & Bretschneider

[57] ABSTRACT

Phenethyl derivatives of thiazole of the formula:

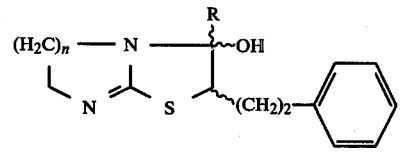

wherein n is 1 or 2 and R is a naphthyl radical, a phenyl radical or a phenyl radical carrying one or more substituents selected from $C_{1-4}$ alkyl, $C_{1-4}$ alkoxy, methylenedioxy and trifluoromethyl radicals and halogen atoms, are useful in therapy in the treatment of depression.

9 Claims, No Drawings

THERAPEUTICALLY USEFUL PHENETHYL DERIVATIVES OF THIAZOLE

DESCRIPTION

The present invention relates to new therapeutically useful phenethyl derivatives of thiazole, to a process for their preparation and pharmaceutical compositions containing them.

The phenethyl derivatives of thiazole of the present invention are those compounds of the general formula:

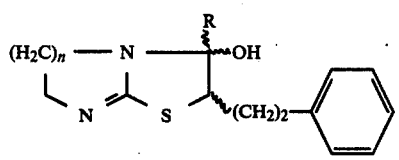

wherein n is 1 or 2 and R is a naphthyl radical, a phenyl radical, or a phenyl radical carrying one or more substituents selected from alkyl and alkoxy radicals, each containing from 1 to 4 carbon atoms, methylenedioxy and trifluoromethyl radicals and halogen atoms, and pharmaceutically acceptable acid addition salts thereof, e.g. the hydrochlorides and hydrobromides.

The compounds of general formula (I) possess centres of asymmetry and can exist in the form of optical isomers and mixtures thereof, e.g. racemates.

Preferably the symbol R represents a naphthyl radical, a phenyl radical or a phenyl radical carrying one or two substituents selected from methyl, methoxy, methylenedioxy and trifluoromethyl radicals and chlorine, bromine and fluorine atoms.

Preferred compounds of general formula (I) are those wherein R represents the phenyl radical carrying a chlorine atom or a methoxy radical in the 3-position or chlorine atoms or methoxy radicals in the 3- and 4-positions. Of outstanding importance are 2-phenethyl-3-(3-chlorophenyl)-2,3,6,7-tetrahydro-5H-thiazolo[3,2-a]pyrimidin-3-ol, 2-phenethyl-3-(3-methoxyphenyl)-2,3,6,7-tetrahydro-5H-thiazolo-[3,2-a]pyrimidin-3-ol, 2-phenethyl-3-(3-chlorophenyl)-2,3,5,6-tetrahydroimidazo[2,1-b]thiazol-3-ol and 2-phenethyl-3-(3,4-dichlorophenyl)-2,3,5,6-tetrahydroimidazo[2,1-b]thiazol-3-ol, and pharmaceutically acceptable acid addition salts of each such compound.

According to a feature of the present invention, the phenethyl derivatives of thiazole of general formula (I) are prepared by the process which comprises reacting imidazolidine-2-thione or 3,4,5,6-tetrahydropyrimidine-2-thiol of the formula:

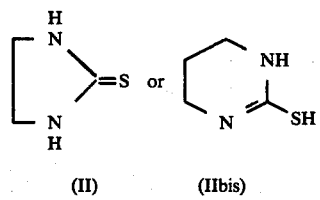

with a ketone of the general formula:

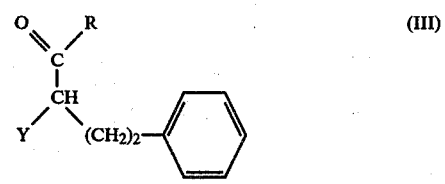

wherein Y represents a bromine or chlorine atom or any other labile group, and R is as hereinbefore defined.

The reaction of the compound (II) or (IIbis) with the compound (III) is carried out in a suitable organic solvent, such as acetone or an alcohol, for example isopropanol.

The ketones which leads to the starting compounds of general formula (III) are obtained either by the conventional reaction of the nitrile with Grignard reagent followed by hydrolysis, for example in accordance with the method described by W. J. Humphlett, M. J. Weiss and C. R. Hauser, J. Amer. Chem. Soc. 70, 4020 (1948), or by reaction of the acid chloride with the Grignard reagent in tetrahydrofuran at −78° C., for example in accordance with the method described by F. Sato, M. Inoue, K. Oguro and M. Sato, Tetrahedron Letters No. 44, pages 4303–4306 (1979), or by oxidation of the corresponding alcohol.

Pharmaceutically acceptable acid addition salts of the phenethyl derivatives of thiazole of general formula (I) can be obtained by methods known per se, for example by reacting a base of formula (I) with an acid, the anion of which is relatively innocuous to the animal organism in therapeutic doses of the salts, e.g. hydrochloric, hydrobromic, methanesulphonic, fumaric or maleic acid.

The following Examples illustrate the preparation of compounds of this invention.

The analyses and the IR and NMR spectra confirm the structure of the compounds.

EXAMPLE 1

2-Phenethyl-3-phenyl-2,3,5,6-tetrahydroimidazo[2,1-b]thiazol-3-ol and its hydrochloride.

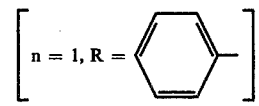

A solution of 25 g (0.082 mol) of α-bromo-(phenylpropyl) phenyl ketone in 200 ml of acetone is added all at once to a solution of 6.3 g (0.0618 mol) of imidazolidine-2-thione in 1 l. of acetone. The mixture is stirred for 20 hours. It is then filtered and the material on the filter is rinsed several times with acetone and then once with diethyl ether. The solid obtained is dried in vacuo. This gives the hydrobromide of the compound, which melts at 140°–141° C.

The hydrobromide is taken up in water and $CH_2Cl_2$. The mixture is shaken and rendered alkaline with $Na_2CO_3$. Extraction is carried out with $CH_2Cl_2$ and the extract is then washed with water, dried over $MgSO_4$ and filtered, and the filtrate is concentrated. The resultant compound is taken up in diisopropyl ether, filtered off and rinsed with this solvent.

The base obtained melts at 148°–150° C.

The hydrochloride is prepared by passing a stream of HCl gas into a solution of 5.6 g (0.017 mol) of the base in a CH2Cl2/MeOH mixture. The melting point of the hydrochloride is 138°-139° C.

EXAMPLE 2

2-Phenethyl-3-(3-chlorophenyl)-2,3,5,6-tetrahydroimidazo-[2,1-b]thiazol-3-ol, and its hydrochloride.

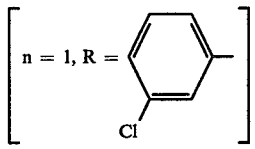

A solution of 28 g (0.083 mol) of α-bromo-(phenylpropyl) 3-chlorophenyl ketone in 200 ml of acetone is added to a solution of 4.3 g (0.042 mol) of imidazolidine-2-thione in 570 ml of acetone. The precipitated product is filtered off and rinsed with acetone and then with diethyl ether. The base is liberated by taking up the hydrobromide salt obtained in a water/chloroform mixture and adding sodium carbonate to pH 9. After extraction with chloroform and washing with water, the product is dried over MgSO4 and filtered and the filtrate is concentrated. The crystalline product is taken up in diethyl ether, filtered off and rinsed with diethyl ether. A stream of hydrogen chloride gas is passed into a solution of 9.1 g of the powder in a 1/1 mixture of MeOH/CH2Cl2. The hydrochloride formed is filtered off, rinsed with diethyl ether and dried in vacuo. The melting point of the hydrochloride is 134-135° C.

EXAMPLE 3

2-Phenethyl-3-(3-chlorophenyl)-2,3,6,7-tetrahydro-5H-thiazolo[3,2-a]pyrimidin-3-ol and its hydrochloride.

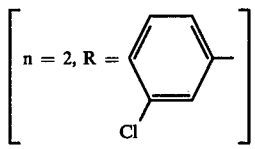

A solution of 28 g (0.083 mol) of αbromo-(phenylpropyl) 3-chlorophenyl ketone in 200 ml of acetone is added to a solution of 4.9 g (0.042 mol) of tetrahydropyrimidine-2-thiol in 800 ml of acetone. The mixture is stirred for one day and filtered and the material on the filter is rinsed with acetone and then with diethyl ether. The hydrobromide formed is taken up in a water/CHCl3 mixture and the base is freed by adding Na2CO3. The base is extracted with chloroform, the extract is washed with water, dried and filtered and the filtrate is concentrated. This gives an oil, which is taken up in diethyl ether. The product crystallises. A stream of HCl gas is passed into a solution of the base in a MeOH/CH2Cl2 mixture, in a bath of iced water. The hydrochloride precipitates on adding diethyl ether. It is filtered off, rinsed with diethyl ether and dried in vacuo. The melting point of the hydrochloride is 177°-178° C.

The Table which follows shows the compounds of the invention which were prepared by way of examples.

TABLE

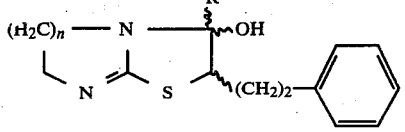

| Compound | n | R | Form | Melting point (0° C.) |
|---|---|---|---|---|
| 1 | 1 | $C_6H_5$ | free base | 148-150 |
| 2 | 1 | $C_6H_5$ | HCl | 138-9 |
| 3 | 1 | 4-Cl—$C_6H_4$ | free base | 161-2 |
| 4 | 1 | 3-Cl—$C_6H_4$ | HCl | 134-5 |
| 5 | 1 | 3,4-$Cl_2$—$C_6H_3$ | HBr | 159-160 |
| 6 | 1 | 2-Me—$C_6H_4$ | HCl | 139-140 |
| 7 | 1 | 2-Cl—$C_6H_4$ | HCl | 155-6 |
| 8 | 1 | 2,3-$Me_2$—$C_6H_3$ | HBr | 142-3 |
| 9 | 1 | 2-F—$C_6H_4$ | HCl | 131-2 |
| 10 | 1 | 3-$CF_3$—$C_6H_4$ | HBr | 144-5 |
| 11 | 1 | α-naphthyl | HBr | 148-148.5 |
| 12 | 1 | 2,4-$Cl_2$—$C_6H_3$ | HBr | 138-140 |
| 13 | 1 | 2-OMe—$C_6H_4$ | HCl | 153-153.5 |
| 14 | 1 | 4-Br—$C_6H_4$ | HCl | 145-6 |
| 15 | 1 | 3,4-$(OMe)_2$—$C_6H_3$ | HCl | 132-3 |
| 16 | 1 | 3,4-$(OCH_2O)$—$C_6H_3$ | HCl | 139-140 |
| 17 | 2 | $C_6H_5$ | free base | 154-5 |
| 18 | 2 | 4-Cl—$C_6H_4$ | free base | 105-7 |
| 19 | 2 | 3-OMe—$C_6H_4$ | HBr | 185-6 |
| 20 | 2 | 2-Me—$C_6H_4$ | HBr | 146-7 |
| 21 | 2 | 2-Cl—$C_6H_4$ | HBr | 199-200 |
| 22 | 2 | 3-Cl—$C_6H_4$ | HCl | 177-8 |
| 23 | 2 | 3,4-$Cl_2$—$C_6H_3$ | HCl | 198-9 |
| 24 | 2 | 3,4-$(OMe)_2$—$C_6H_3$ | HBr | 208-9 |
| 25 | 2 | 3,4-$(OCH_2O)$—$C_6H_3$ | HBr | 196.5-7.5 |
| 26 | 2 | 4-OMe—$C_6H_4$ | HBr | 192-3 |
| 27 | 2 | 4-Me—$C_6H_4$ | HBr | 187-8 |

The compounds of general formula (I) of the present invention were subjected to pharmacological experiments, which showed their antidepressive activity.

The toxicity of the compounds was determined on mice by intraperitoneal administration. The LD 50 ranges from 100 to >1000 mg/kg animal body weight.

The antidepressive activity was determined in accordance with the test for the antagonism towards the ptosis caused by reserpine (C. Gouret et al., J. Pharmacol. (Paris) 8, 333-350 [1977]).

The mice (male, CD1 Charles River, France, 18-22 g) simultaneously receive the products to be studied or the solvent (administered intraperitoneally), and the reserpine (4 mg/kg, administered subcutaneously).

After sixty minutes, the degree of palpebral ptosis is estimated for each mouse by means of a rating scale (0 to 4).

The average rating and the percentage variation, relative to the control batch, are calculated for each dose.

The AD 50, or the dose which reduces the average ptosis score by 50%, relative to the control animals, is determined graphically for each product.

The AD 50 varies from 1 to 5 mg/kg animal body weight, administered intraperitoneally.

The pharmacological results show that the compounds of the invention can be useful for the treatment of depression.

The compounds of the invention can be presented in any form suitable for oral or parenteral administration, for example in the form of tablets, coated tablets, gelatin capsules, solutions to be taken orally or injected, or the like, in association with any suitable excipient.

The daily dosage for an adult can range from 5 to 200 mg.

I claim:

1. Phenethyl derivatives or thiazole, and their optical isomers, of the formula:

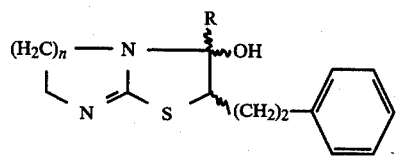

wherein n is 1 or 2, and R is naphthyl, phenyl, or phenyl carrying one or more substituents selected from alkyl radicals of 1 through 4 carbon atoms, alkoxy radicals of 1 through 4 carbon atoms, methylenedioxy and trifluoromethyl radicals and halogen atoms, and pharmaceutically acceptable acid addition salts thereof.

2. Compounds according to claim 1 wherein R represents naphthyl, phenyl, or phenyl carrying one or two substituents selected from methyl, methoxy, methylenedioxy and trifluoromethyl radicals and chlorine, bromine and fluorine atoms.

3. Compounds according to claim 1 wherein R represents phenyl carrying a chlorine atom or a methoxy radical in the 3-position or chlorine atoms or methoxy radicals in the 3- and 4-positions.

4. A compound according to claim 1 which is 2-phenethyl-3-(3-chlorophenyl)-2,3,6,7-tetrahydro-5H-thiazolo[3,2-a]pyrimidin-3-ol, and its pharmaceutically acceptable acid addition salts.

5. A compound according to claim 1 which is 2-phenethyl-3-(3-methoxyphenyl)-2,3,6,7-tetrahydro-5H-thiazolo[3,2-a]pyrimidin-3-ol, and its pharmaceutically acceptable acid addition salts.

6. A compound according to claim 1 which is 2-phenethyl-3-(3-chlorophenyl)-2,3,5,6-tetrahydroimidazo-[2,1-b]thiazol-3-ol, and its pharmaceutically acceptable acid addition salts.

7. A compound according to claim 1 which is 2-phenethyl-3-(3,4-dichlorophenyl)-2,3,5,6-tetrahydroimidazo-[2,1-b]thiazol-3-ol, and its pharmaceutically acceptable acid addition salts.

8. A pharmaceutical composition for the treatment of depression containing a dose effective for treatment of depression of a compound claimed in claim 1.

9. A method for the treatment of a patient suffering from depression which comprises administering to such patient an amount of a phenethyl derivative of thiazole of the general formula depicted in claim 1, or a pharmaceutically acceptable acid addition salt thereof, effective to relieve the depression.

* * * * *